US012588938B2

(12) United States Patent (10) Patent No.: US 12,588,938 B2
Zhang et al. (45) Date of Patent: Mar. 31, 2026

(54) COMBINATION PROBE FOR CRYOABLATION AND THERMAL ABLATION AND RELATED METHODS

(71) Applicant: Varian Medical Systems, Inc., Palo Alto, CA (US)

(72) Inventors: Hongxuan Zhang, Austin, TX (US); Vineel Vallapureddy, Plymouth, MN (US); Ryan Medema, Georgetown, TX (US); Sean Doll, Cedar Park, TX (US); Elizabeth Campo, Austin, TX (US); Kenneth Zapalac, Cedar Park, TX (US)

(73) Assignee: Varian Medical Systems, Inc., Palo Alto, CA (US)

( * ) Notice: Subject to any disclaimer, the term of this patent is extended or adjusted under 35 U.S.C. 154(b) by 410 days.

(21) Appl. No.: 18/186,527

(22) Filed: Mar. 20, 2023

(65) Prior Publication Data

US 2024/0315750 A1 Sep. 26, 2024

(51) Int. Cl.
*A61B 18/02* (2006.01)
*A61B 18/00* (2006.01)

(52) U.S. Cl.
CPC .... *A61B 18/02* (2013.01); *A61B 2018/00041* (2013.01); *A61B 2018/00577* (2013.01); *A61B 2018/0262* (2013.01)

(58) Field of Classification Search
CPC .................. A61B 18/02; A61B 18/082; A61B 2018/00041; A61B 2018/00577; A61B 2018/0262; A61B 2018/00994; A61B 2018/0293
See application file for complete search history.

(56) References Cited

U.S. PATENT DOCUMENTS

| | | | |
|---|---|---|---|
| 3,971,383 A | 7/1976 | van Gerven | |
| 4,202,336 A | 5/1980 | van Gerven | |
| 7,846,154 B2 | 12/2010 | Bliweis | |
| 2002/0151946 A1* | 10/2002 | Dobak, III | A61B 18/02 607/105 |
| 2002/0198578 A1* | 12/2002 | Dobak, III | A61F 7/12 607/104 |

(Continued)

FOREIGN PATENT DOCUMENTS

| | | |
|---|---|---|
| WO | 2007075930 A2 | 7/2007 |
| WO | 2011142909 A1 | 11/2011 |

(Continued)

OTHER PUBLICATIONS

PCT International Search Report and Written Opinion issued for corresponding PCT Application No. PCT/US2024/017846 dated Jun. 7, 2024, 18 pages.

*Primary Examiner* — Ankit D Tejani
*Assistant Examiner* — Joshua Brendon Solomon
(74) *Attorney, Agent, or Firm* — Morgan, Lewis & Bockius LLP; Manita Rawat

(57) ABSTRACT

A combination ablation probe includes a shell configured to be positioned at a target tissue in a patient and a conduit positioned inside the shell. The conduit is configured to supply a cryo-fluid toward a tip of the probe. The probe also includes a heater positioned radially outward of the conduit in the shell and at least one heat transfer element in thermal communication with the heater and the shell.

20 Claims, 7 Drawing Sheets

(56)          References Cited

U.S. PATENT DOCUMENTS

2014/0214140 A1*   7/2014   Ginsburg ................ A61F 7/123
                                                                  607/113
2014/0275767 A1       9/2014   Baust
2019/0053842 A1*   2/2019   Shadduck ............... A61M 5/31
2019/0328437 A1*   10/2019   Perron ................... A61B 18/02

FOREIGN PATENT DOCUMENTS

WO          2020163854  A1       8/2020
WO          2024196558  A1       9/2024

* cited by examiner

COMBINATION PROBE FOR CRYOABLATION AND THERMAL ABLATION AND RELATED METHODS

FIELD

The present disclosure relates to apparatuses and methods for performing cryoablation and thermal ablation. More particularly, the present disclosure relates to a probe for performing procedures that may include both cryoablation and thermal ablation.

BACKGROUND

This section provides background information related to the present disclosure which is not necessarily prior art.

Systems and methods for providing ablation treatments may include probes that are introduced at or near target tissue in a patient. In traditional systems, a probe may be used in a cryoablation procedure. The probe may be coupled to a cryoablation system. The cryoablation system may include an extremely cold cryo-fluid (liquid, gas, or mixed phase) that may be passed to the probe in thermal contact with the target tissue. Heat from the tissue passes from the tissue, through the probe, and into the fluid that removes heat from the targeted tissue. This removal of heat causes tissue to freeze, resulting in the destruction of the targeted tissue. The cryo-fluid may also be heated subsequent to the freezing cycle. The heating may thaw the frozen tissue to allow the cryoprobe to be removed from the tissue.

Traditional probes may also be used for thermal ablation. The probe used for thermal ablation may include, for example, an RF antenna or a microwave antenna that can be supplied with a suitable power signal to cause tissue at or near the probe to be heated to sufficient temperatures to destroy the target tissue. Traditional or existing probes do not include elements to permit both cryoablation and thermal ablation to be performed by a common probe. In some existing methods, two or more probes must be inserted at the site of the target tissue if different ablation methods are to be performed. There exists a need, therefore, for improved systems, probes, and methods that can allow cryoablation and thermal ablation to be performed by a common probe.

SUMMARY

This section provides a general summary of the disclosure, and is not a comprehensive disclosure of its full scope or all of its features.

In some embodiments of the present disclosure, a combination ablation probe is provided. The combination ablation probe can be operated to perform cryo cycle and thermal cycles. Both the cryo cycle and the thermal cycle can be ablation cycles that cause the destruction of a target tissue in a patient. The combination probes of the present disclosure may include a heater located internal to the probe that can achieve thermal ablation temperatures. The heater may be thermally coupled to a heat transfer element that can transfer thermal energy from the heater to the shell of the combination probe. The heat transfer element may be further configured to allow for the flow of cryo-fluid away from the distal end of the probe in a return pathway.

In some embodiments, an ablation probe may include a shell configured to be positioned at a target tissue in a patient and a conduit positioned inside the shell. The conduit may be configured to supply a cryo-fluid toward a tip of the probe. The probe may also include a heater positioned radially outward of the conduit in the shell and at least one heat transfer element in thermal communication with the heater and the shell.

In one aspect, the at least one heat transfer element may be positioned radially outward of the conduit and radially inward of the shell.

In another aspect, the conduit may include at least one opening at or near the tip to allow cryo-fluid to exit the interior of the conduit and flow in a return direction between an outer surface of the conduit and an inner surface of the shell.

In another aspect, the at least one heat transfer element may be positioned on the outer surface of the conduit spaced apart from the at least one opening of the conduit.

In another aspect, the at least one heat transfer element may be directly in contact with the heater and a distal end of the tip.

In another aspect, the at least one heat transfer element may be positioned in direct contact with the heater and the shell.

In another aspect, the at least one heat transfer element may include a conical plug positioned at the tip.

In another aspect, the at least one heat transfer element may include an annular member positioned at a predetermined axial location along an outer surface of the conduit.

In another aspect, conductive portions of the annular member may contact an inner surface of the shell. The conductive portions are spaced apart from each other around a circumference of the annular member to define return pathways for the cryo fluid to flow away from the tip toward a proximal end of the ablation probe.

In another aspect, the at least one heat transfer element may include a plurality of annular members positioned along an outer surface of the conduit and each annular member of the plurality of annular members is spaced apart from an adjacent annular member.

In another aspect, the heater may include a resistive heating coil.

In another aspect, the resistive heating coil may be in direct contact with the heat transfer element and not in direct contact with the shell.

In another aspect, the heater may be coiled around the at least one heat transfer element.

In another aspect, the at least one heat transfer element may include an arcuate shaped member positioned around a portion of an outer circumference of the conduit.

In another aspect, the heater may be coiled around the arcuate shaped member.

In some embodiments in accordance with the present disclosure, an ablation probe may include an outer shell and an inner conduit axially aligned with the outer shell and positioned radially inside the shell. The probe may also include a first annular heat transfer element positioned at a first axial location. The first annular heat transfer element may have an outer profile that includes contacting portions that contact an inner surface of the outer shell and non-contacting portions that are spaced apart from the inner surface of the outer shell. The probe may also include a second annular heat transfer element positioned at a second axial location. The second annular heat transfer element oriented generally parallel to the first annular heat transfer element. The probe may also include a heater positioned inside the shell in contact with the first annular heat transfer element and the second heat transfer element.

In accordance with some embodiments of the present disclosure a method of performing an ablation treatment is provided. The method may include positioning an ablation probe at or near a target tissue in a patient. The method may also include cooling the ablation probe using a cryo-fluid circulated through the ablation probe to cause an ice ball to be formed at the target tissue and heating the ablation probe using a heater positioned inside the ablation probe to cause tissue at or near the target tissue to be destroyed.

In one aspect, the step of heating the ablation probe may include heating the ablation probe to a temperature greater than or equal to 150° C.

In another aspect, the ablation probe is not moved after the ablation probe is positioned at or near the target tissue.

In another aspect, the step of heating the ablation probe may be performed by energizing the heater and conducting heat from the heater through a heat transfer element to an outer shell of the ablation probe.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
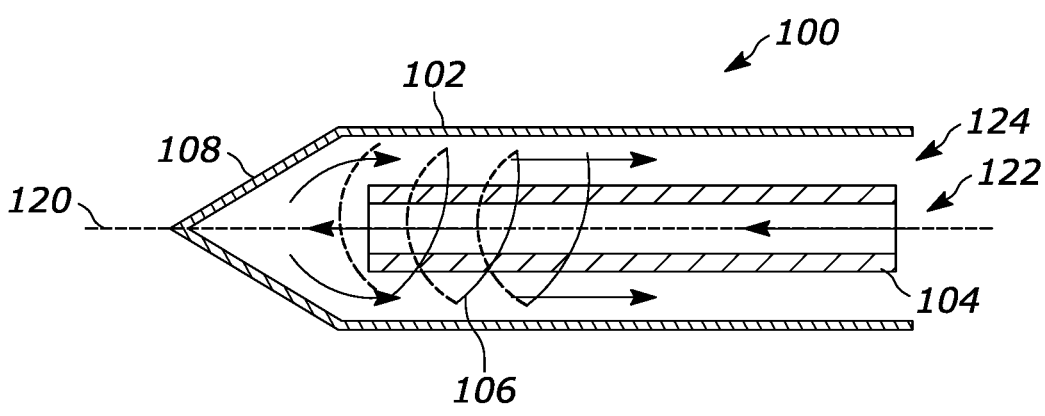
FIG. 1 is a cross-sectional side view of an example ablation probe in accordance with some embodiments of the present disclosure.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

In various embodiments of the present disclosure, improved ablation probes are provided that incorporate elements that allow the same probe to be used for both cryoablation and thermal ablation. Existing probes are typically limited to use for either cryoablation or thermal ablation but not both. In addition, the extended time for heating cycles of existing probes can dessicate tissues which can result in reduced treatment effectiveness. Still further, existing probes and methods also typically require subsequent procedures that follow ablation procedures because the tissues at the ablation site cannot be returned to sufficient temperatures to perform the follow-up procedure at the same time as the ablation treatment. For example, if a target tissue is located at or near a bone or other support structure of a patient, the structural integrity of the bone or support structure can be compromised when the bone or support structure is subjected to the low temperatures of a cryoablation cycle. Without subsequent treatment, the bone or support structure may fail. A cement or other repair substance may be applied to the bone or support structure to address this condition. Such application of cement or repair substance is applied in a follow-up or subsequent treatment because the tissues typically must be returned to normal body temperatures before the cement or repair substance can be applied. The combination probes of the present disclosure can bring tissues back to normal body temperatures more quickly than existing probes and methods so that the follow-up or repair procedure can be performed in the same session as the ablation treatment.

The combination probes of the present disclosure are improvements over existing probes because the probe can be used for cryoablation and/or thermal ablation without the need to insert a second probe at the target tissue in the patient and can be operated at a range of temperatures greater than in existing probes. Furthermore, the elevated levels of temperature that can be achieved for thermal ablation can also be used for other purposes such as coagulation, cauterization, thawing or other purposes. The combination probes of the present disclosure can achieve higher temperatures than existing cryoablation probes such that the secondary or other purposes such as coagulation, cauterization, thawing and the like can be performed more quickly. This provides improved performance over prior art probes by reducing the overall time required for the ablation procedure to reduce risk and improve patient recovery.

The temperatures required to perform various procedures and/or to achieve desired results may vary according to the types of tissues and/or for bodily structures that may be present at or near a target tissue. In the context of tumors or other undesirable tissues that may be present in a patient, such as for cancer tissue therapy or the like, the cryo and thermal ablation temperature range can span a range from −75° C. to +150° C. The combination probes of the present disclosure can be operated in such a temperature range to achieve desirable temperatures for both cryoablation and thermal ablation. In some examples, the combination probes of the present disclosure can be operated at or below −75° C. during cryoablation cycles to grow ice at a target tissue. The same combination probes of the present disclosure may also be operated at a temperature at or above +150° C. to perform thermal ablation. In still other examples, some ablation probes of the present disclosure can be operated at a temperature at or above +200° C. to perform thermal ablation. In still other examples, other operating temperatures ranges can be achieved.

The combination probes of the present disclosure may also be operated at intermediate temperatures between the cryoablation and the thermal ablation temperatures described above. For example, some example combination ablation probes of the present disclosure can be operated at or near a temperature between about 0° C. and about 20° C. to perform thaw cycles to assist in the removal of the combination probe from an ice ball formed during a cryoablation procedure. In other examples, some combination probes of the present disclosure may be operated at or near a temperature of about 80° C. to about 150° C. to perform a coagulation or cauterization cycle. Such cycles may be used to mitigate, reduce, and/or prevent bleeding that may otherwise occur during or after an ablation procedure.

Referring now to FIG. 1, an example ablation probe 100 is shown. The probe 100 may be used to perform an ablation procedure. The probe 100 may be used to perform ablation procedures that may include both a cryoablation cycle and a thermal ablation cycle. The ablation probe 100 may be positioned at or near a target tissue of patient. The target tissue may be an abnormal or undesirable tissue such as a tumor or other growth.

In the example shown, the probe 100 may include an outer shell 102. The shell 102 may be formed from a thin walled tube that extends from a proximal end at or near a handle (not shown) that can be used by an operator to position the probe 100 at the desired position. The probe 100 may extend from the proximal end to a distal end 108 at a tip of the probe 100. The tip of the probe may be pointed to assist in piercing tissue when the probe 100 is positioned at or near the target tissue in the patient.

The shell 102 may form an inner cavity in which the other elements of the probe 100 can be positioned. In this example, the shell 102 has a circular or rounded cross-section that is axially aligned along axis 120. The shell 102 may be formed of any suitable material such as stainless steel or any material having good thermal conductive characteristics and bio-compatibility characteristics. A conduit 104 may be positioned inside the shell 102. The conduit 104 may be a tubular structure that is axially aligned along the axis 120. The conduit 104 can be used to form a pathway for a cryo-fluid to flow into and out of the probe 100. The conduit 104 may include an inner channel 122 that is located inside the conduit 104 that is defined by the inner surface of the conduit 104. The conduit 104 may also define a return channel 124 that is defined by the outer surface of the conduit 104 and the inner surface of the shell 102. The cryo-fluid may flow into the probe 100 through the inner channel 122 and out of the probe 100 through the return channel 124 as shown by the arrows on FIG. 1. The cryo-fluid may exit the conduit 104 through an opening at the distal end of the conduit 104.

The cryo-fluid can be supplied by a suitable cryo-fluid source that can supply the cryo-fluid to the probe 100 during a cryoablation cycle. During such a cryoablation cycle the cryo-fluid can flow into the probe 100 and out of the inner channel 122 at or near the distal end 108 of the probe. In some examples, the probe 100 can be configured as a Joule-Thompson cryoablation probe in which the cryo-fluid expands at the distal end 108 causing a rapid drop in temperature of the cryo-fluid. The cryo-fluid can cause the temperature of the shell 102 to rapidly drop removing thermal energy from the tissue surrounding the probe 100. An ice ball may form at the distal end 108 of the probe 100 to destroy target tissue at the distal end 108 of the probe 100.

In other examples, the probe 100 may be configured as other types of cryoablation probes such as supercritical, near critical, or other type of cryoablation probe to cause ice to form at the target tissue.

During the cryoablation cycle, the cryo-fluid may flow away from the distal end 108 of the probe 100 through the return channel 124. The return channel 124 may have an annular shape positioned radially outward of the conduit 104. The cryo-fluid may be any suitable fluid, gas, or combination of fluid and gas that can be operated at temperatures sufficient to cause ice to form at the probe in a sufficient time frame to support cryoablation procedures. In various examples, the cryo-fluid may be argon, nitrogen, helium, or the like.

As further shown in FIG. 1, the probe 100 may also include heater 106. The heater 106, in the example shown, is a resistive heating coil that is coiled or wound within the shell 102. The heater 106 may be coiled around the conduit 104, for example. The heater 106 may be coiled in a concentric alignment with the conduit 104 and/or the shell 102. In such an arrangement, the heater is aligned along the axis 120. In other examples, the heater may be coiled around the heat transfer element as will be further described.

The heater 106 can be made of a suitable resistive wire that can heat when a current is supplied. The heater 106 can be coupled to a suitable power supply located outside of the probe 100. Suitable wire leads can be positioned, embedded, or otherwise formed in the probe 100 to couple the heater 106 to the power supply (not shown). During a heating or thermal ablation cycle, a power signal can be supplied to the heater 106 to raise the temperature of the heater 106. The heater 106 can raise the temperature of the shell 102 to conduct heat to the target tissue that may be located at or near the probe 100. The temperature can be raised to a temperature sufficient to thermally ablate the target tissue. In some examples, this temperature is at or greater than 150° C. In other examples, the shell 102 of the probe 100 can reach temperatures of 200° C. or greater.

Existing or traditional probes may include a heater to assist with the heating of cryo-fluid. The heating of the cryo-fluid in such traditional probes may assist in a thaw cycle to improve the speed at which the probe may be withdrawn from the ice ball that is formed during the cryoablation cycle. Such traditional probes cannot reach thermal ablation temperatures such as example probe 100 and the other combination ablation probes described in the present disclosure. The probe 100 and others described herein may thermally conduct heat from the heater 106 to the target tissue to cause thermal ablation at the location of the probe 100. In addition, the probe 100 can be operated to heat the localized area of the probe 100 for thermal ablation without the existence or flow of a fluid inside in the probe 100. Still further, a thaw cycle or other heated cycles can be more rapidly performed using the probes of the present disclosure because of the increased heating capacity and heating functionality of the combination probes of the present disclosure.

Figure 2:
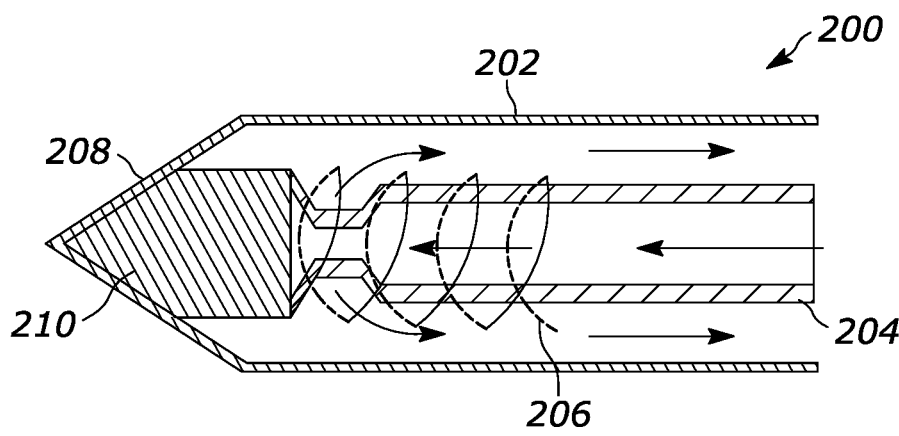
FIG. 2 is a cross-sectional side view of another example ablation probe in accordance with some embodiments of the present disclosure.

Referring now to FIG. 2, another example probe 200 is shown. The example probe 200 may include a shell 202, a conduit 204, and a heater 206. The probe 200 may use these features to operate as described above with respect to probe 100. The shell 202, the conduit 204, and the heater 206 may be configured and positioned as previously described to allow the probe 200 to operate and perform both cryo-ablation cycles and thermal ablation cycles. Such description is not repeated here for the sake of brevity.

The example probe 200 also includes a tip plug 210. The tip plug 210 may be positioned at the distal end 208 of the shell 202. The tip plug 210 can thermally couple the heater 206 to the shell 202. The tip plug 210 can be connected to both the heater 206 and to the shell 202 to conduct heat from the heater 206 to the shell 202. The tip plug 210 can have a cone shape that is complimentarily shaped to the internal cavity of the probe 200 at the distal end 208. In this manner, the tip plug 210 may have an external surface area that is aligned with and contacts an internal surface of the shell 202. The tip plug 210 can be made of thermally conductive material to efficiently conduct heat from the heater 206 to the shell 202. One or more coils of the heater 206 may be coiled around the tip plug 210. In this example, the tip of the shell 202 may be heated to elevated temperatures for thermal ablation of tissue. The internal chambers of the probe 200 may be devoid of cryo-fluid during the heating of the probe 200 during a thermal ablation cycle.

Figure 3:
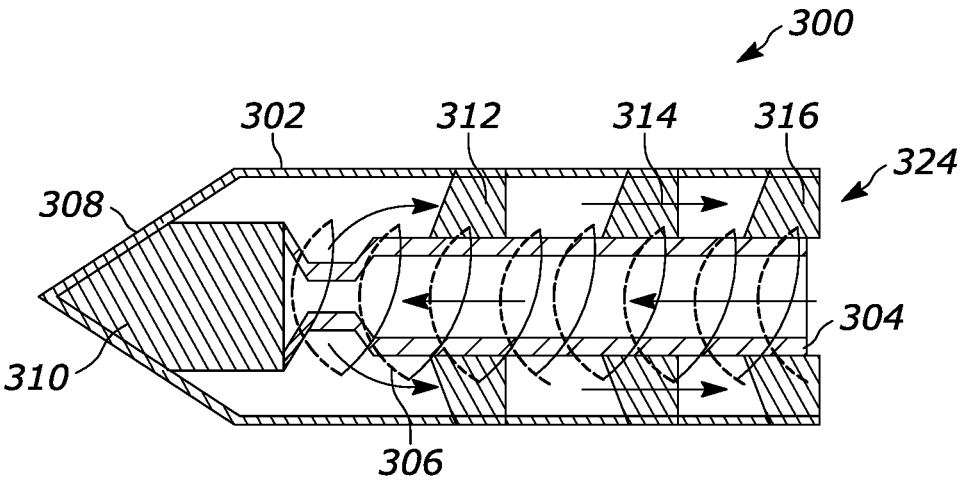
FIG. 3 is a cross-sectional side view of another example ablation probe in accordance with some embodiments of the present disclosure.

Another example ablation probe 300 is shown in FIG. 3. The probe 300 is similar to the ablation probe 200 previously described. As shown, the probe 300 may include a shell 302, a conduit 304, a heater 306, and a tip plug 310. These elements may be positioned and configured similarly to the probe 100 and/or the probe 200 previously described. For the sake of brevity, such description is not repeated but it should be appreciated that the probe 300 can be similarly configured.

The ablation probe 300 may also include a first heat transfer element 312, a second heat transfer element 314 and a third heat transfer element 316. The first heat transfer element 312, the second heat transfer element 314, and the third heat transfer element 316 can each have a similar cross-sectional shape. The first heat transfer element 312, the second heat transfer element 314, and the third heat transfer element 316 may each be positioned radially outward of the conduit 304 but inside the shell 302. The first heat transfer element 312, the second heat transfer element 314, and the third heat transfer element 316 may each also be connected to the heater 306. In this manner, the first heat transfer element 312, the second heat transfer element 314, and the third heat transfer element 316 may each be in thermal communication between the heater 306 and the shell 302. The first heat transfer element 312, the second heat transfer element 314, and the third heat transfer element 316 can operate to conduct heat from the heater 306 to the shell 302.

In the example shown, the probe includes three heat transfer elements spaced apart from one another and positioned generally parallel to each other. The heat transfer elements may also be spaced axially from an opening in the conduit 304 through which the cryo-fluid may exit the conduit 304 before moving through return channel 324. In other examples, other quantities of heat transfer elements may be used to transfer heat from the heater 306 to the shell 302. In such examples, the number of heat transfer elements may be less than three elements. In other examples, the number of heat transfer elements may be greater than three elements. The number of heat transfer elements and the position thereof may be chosen and positioned so as to provide an ablation zone of a predetermined size on the ablation probe 300. For example, if a larger ablation zone is desired, more than three heat transfer elements may be used. The heater 306 can be similarly varied in axial length so as to provide heating to each of the heat transfer elements.

In a similar manner to that previously described, the probe 300 can be operated to perform a cryoablation cycle. During a cryoablation cycle, a cryo-fluid can be supplied via the conduit 304 to the distal end 308 of the probe 100. The cryo-fluid can be of sufficient temperature to rapidly remove heat from the tissue surrounding or near the probe 100. The cryo-fluid may then flow away from the distal end 308 via the return channel 324 that is located between an outer surface of the conduit 304 and the inner surface of the shell 302. While it may appear in FIG. 3 that the return channel 324 is obstructed by the first heat transfer element 312, the second heat transfer element 314, and/or the third heat transfer element 316, a return flow path is provided by openings, gaps, or other spaces defined between each of the first heat transfer element 312, the second heat transfer element 314, and the third heat transfer element 316 and the inner surface of the shell 302.

Figure 4:
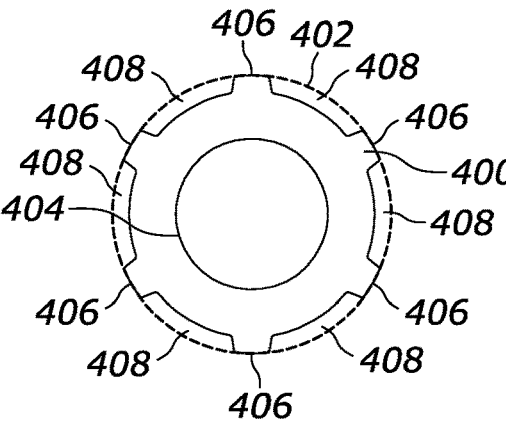
FIG. 4 is a cross-sectional end view of an example heat transfer element that can be used in various ablation probes of the present disclosure.

An example heat transfer element 400 is shown in FIG. 4. The first heat transfer element 312, the second heat transfer element 314, and the third heat transfer element 316 may each have an outer profile such as the one shown in FIG. 4. In this example, the heat transfer element 400 has an outer profile that is configured so that portions of the heat transfer element 400 contact the inner surface 402 of the shell. Other portions between the contacting portions are spaced apart from the inner surface 402 of the shell. The spaced portions define return flow openings 408 that are positioned around the heat transfer element 400 to allow cryo-fluid to flow away from the distal end 308 of the probe 300.

In this example, the heat transfer element 400 has an annular shape that allows the inner opening 404 to be positioned radially outward of the conduit 304. Each of the heat transfer elements 400 can be positioned and/or slid over the conduit 304 and secured at a desired axial position on the conduit 304 using a suitable attachment such as adhesive, epoxy, staking, crimping, or the like. The heat transfer element 400 can have a gear-like outer profile that includes one or more conductive or contacting portions 406 positioned around the circumference of the heat transfer element 400. The outer diameter of the contacting portions 406 can be sized so as to contact the inner surface 402 of the shell. At the portions of the heat transfer element 400 that are spaced apart from the inner surface 402 of the shell, the outer diameter of the heat transfer element 400 can be less than the diameter of the inner surface 402 of the shell to define the return pathways 408.

In the example shown, the heat transfer element 400 includes six equally spaced contacting portions 406. The contacting portions 406 may have a width (measured along the circumference of each contacting portion as an arc-length) that is about one-third the width of the return pathways 408 positioned between each contacting portion 406. In other examples, the contacting portions 406 and the return pathways 408 can have other relative sizes.

As previously discussed, each of the first heat transfer element 312, the second heat transfer element 314, and the third heat transfer element 316 may have a profile as shown in FIG. 4. The contacting portions 406 of the adjacent heat transfer elements may be aligned longitudinally or may be offset. Thus, the cryo-fluid may or may not follow a linear path as it travels away from the distal end 308. The cryo-fluid may wind its way over and around the various return pathways 408 of each heat transfer element 400 if more than one heat transfer element 400 is used in the ablation probe 300. The offsetting of the contacting portions 406 of the heat transfer element promotes mixing of the cryo-fluid to obtain a more uniform heating/cooling profile along the longitudinal axis of the probe if desired.

Figure 5:
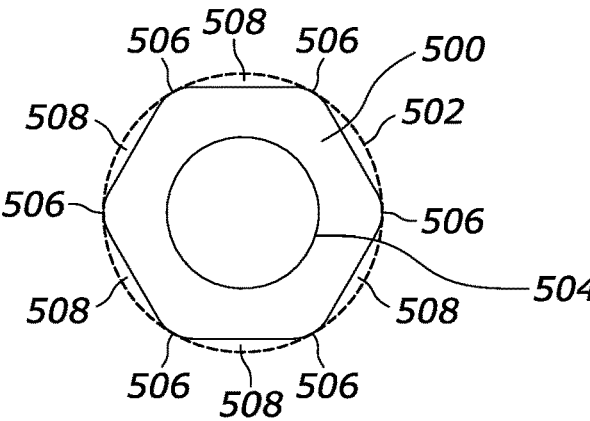
FIG. 5 is a cross-sectional end view of another example heat transfer element that can be used in various ablation probes of the present disclosure.

Another example heat transfer element 500 is shown in FIG. 5. The first heat transfer element 312, the second heat transfer element 314, and the third heat transfer element 316 may each have an outer profile such as the one shown in FIG. 5. In other examples, more than three heat transfer elements 500 or less than three heat transfer elements 500 may be used in an ablation probe. The heat transfer element 500 included contacting portions 506 that may contact the inner surface 502 of the shell. The contacting portions 506 may facilitate the conductive transfer of heat from the heater to the shell. The heat transfer element 500 may also be spaced apart from the inner surface 502 of the shell at various locations around the circumference of the heat transfer element 500. These spaced apart regions may define return pathways 508 through which cryo-fluid may flow during its circulation through the ablation probe during a cryoablation cycle.

As further shown, the heat transfer element 500 may have an outer profile that is hexagonally shaped with six sides of equal size. The vertexes of the sides of the outer profile may be rounded or have a smooth radius at the contacting portions 506. The rounded contacting portions 506 may have a radius that corresponds and/or is equal to the diameter of the inner surface 502 of the shell. In other examples, the outer profile of the heat transfer element 500 may have other shapes such as an octagon, pentagon, or other outer profiles with various numbers of sides that may be greater than six sides or less than six sides.

The heat transfer element 500 may also have an inner opening 504 that can be used to position the heat transfer element 500 on the conduit in the ablation probe. The heat transfer element 500 can be positioned and/or fixed in a desired axial position in the ablation probe along the longitudinal axis as previously described with respect to the heat transfer element 400.

Figure 6:
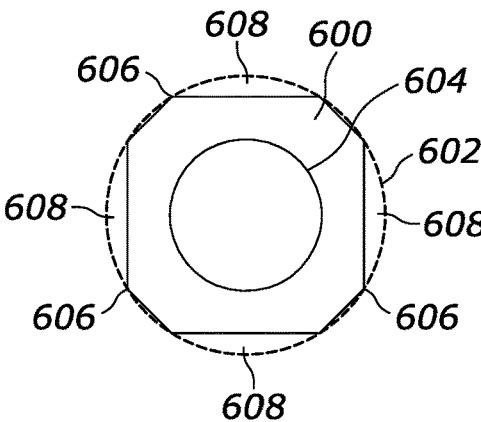
FIG. 6 is a cross-sectional end view of another example heat transfer element that can be used in various ablation probes of the present disclosure.

Another example heat transfer element 600 is shown in FIG. 6. The first heat transfer element 312, the second heat transfer element 314, and the third heat transfer element 316 may each have an outer profile such as the one shown in FIG. 6. In other examples, more than three heat transfer elements 600 or less than three heat transfer elements 600 may be used in an ablation probe. The contacting portions 606 may facilitate the conductive transfer of heat from the heater to the shell. The heat transfer element 600 may also be spaced apart from the inner surface 602 of the shell at various locations around the circumference of the heat transfer element 600. These spaced apart regions may define return pathways 608 through which cryo-fluid may flow during its circulation through the ablation probe during a cryoablation cycle.

As shown, the heat transfer element 600 may have a modified square outer profile. Other outer profiles can also be used. The corners of the square shape may be truncated and/or rounded so that the contacting portions 606 have a shape complimentary to the shape of the inner surface 602. The heat transfer element 600 may also have an inner opening 604 that can be used to position the heat transfer element 600 at a position that is radially outward of the conduit. The heat transfer element 600 can be positioned and/or fixed at a desired axial position along the conduit using adhesive, epoxy, or other mechanical attachment as previously described.

Figure 7:
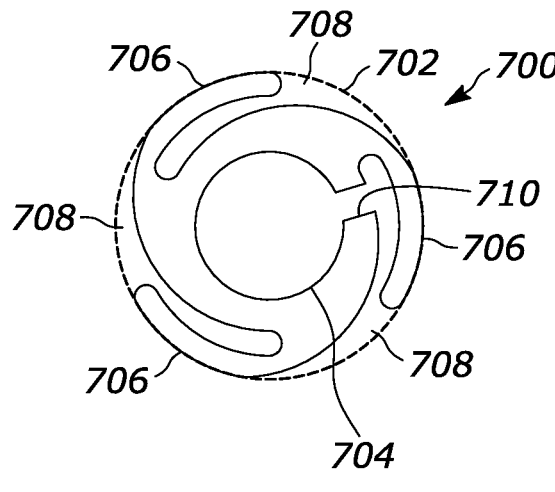
FIG. 7 is a cross-sectional end view of another example heat transfer element that can be used in various ablation probes of the present disclosure.

Another example heat transfer element 700 is shown in FIG. 7. The first heat transfer element 312, the second heat transfer element 314, and the third heat transfer element 316 may each have an outer profile such as the one shown in FIG. 7. In various example ablation probes, the probe may include one or two or more heat transfer elements 700. The heat transfer element 700, in this example, has contacting portions 706 that extend circumferentially relative to a center of the element. Each contacting portion 706 may be flexible so that the contacting portion is moved radially inward when the heat transfer element 700 is positioned inside the inner surface 702 of the shell. In this manner, a biasing force of each contacting portion 706 may keep each contacting portion 706 in contact with the inner surface 702 of the shell.

As further shown, each contacting portion 706 may be configured as a circumferentially extending finger that is spaced away from a center portion of the heat transfer element 700. In this manner, the return pathways 708 not only include regions that are located between each of the contacting portions 706 but also regions radially inward of each contacting portion 706 that are located between the contacting portion 706 and the center portion of the heat transfer element 700. This type of configuration may allow the return pathways 708 to have a larger cross-sectional area than may otherwise be possible using other shaped contacting portions to allow increased fluid flow if desired.

As further shown, the heat transfer element 700 may have a notch 710 positioned at a center portion of the heat transfer element 700. The notch 710 can allow the diameter of the inner opening 704 to expand in response to thermal expansion, or in response to hydraulic forces. The heat transfer element 700 can be installed on the conduit of the ablation probe. The inner opening 704 may have a diameter that is smaller than the outer diameter of the conduit. The notch 710 may allow the inner opening 704 to expand so that the heat transfer element 700 may be retained in a desired position by an interference fit. As can be appreciated, other heat transfer elements of the present disclosure, such as elements 400, 500, 600 may also have a similar notch to allow for similar interference fits and/or to aid in the installation of the heat transfer element in the ablation probe.

The heat transfer elements of the present disclosure can be made of various suitable materials. The material is thermally conductive to allow heat to be efficiently conducted from the heater through the heat transfer element(s) to the shell. Various suitable materials include aluminum, brass, silver, and beryllium copper due to the advantageous properties of high thermal conductivity and high coefficients of thermal expansion. Aluminum and silver may be preferable due to their lower cost and performance over other materials.

The material preferably also has a coefficient of thermal expansion that is compatible with the other elements of the ablation probe. The coefficient of thermal expansion is preferably within a predetermined range of the coefficient of thermal expansion of the materials of the conduit and/or the shell. Since the ablation probe is operated in a wide range of operating temperatures (e.g., about −50° C. to about 200° C.), the thermal expansion of the heat transfer element preferably does not cause interference with or unduly restrict the flow of cryo-fluid and/or cause undesirable contact between adjacent component at any of the operating temperatures. In some embodiments, the material of the heat transfer elements has a coefficient of thermal expansion which is higher than the coefficient of thermal expansion of the shell of the probe, and in such embodiments when the probe is operated in a heating mode the heat transfer elements will expand more than the shell causing increased pressure between the heat transfer elements and the shell. This may provide increased contact between the heat transfer elements and the shell and/or increased transfer of heat from the heat transfer elements to the shell.

Figure 8:
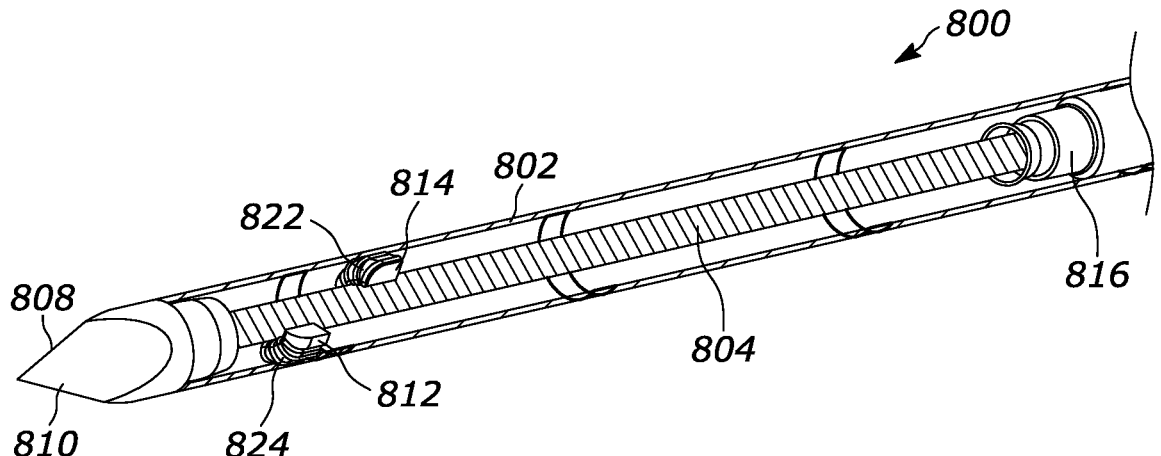
FIG. 8 is a cut-away isometric view of an example ablation probe that includes another example heat transfer element in accordance with some embodiments of the present disclosure.
Figure 9:
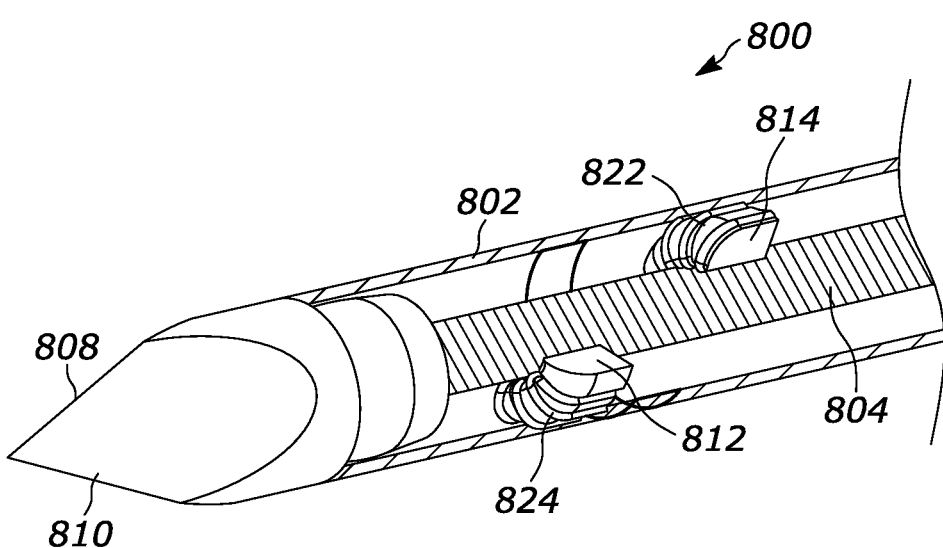
FIG. 9 is an enlarged view of the tip portion of the example ablation probe of FIG. 8.

Another example ablation probe 800 is shown in FIGS. 8 and 9. The probe 800 includes a shell 802, a conduit 804, a first heat transfer element 812, a second heat transfer element 814, a first heater 824 and a second heater 822. The probe 800 can operate in both a cryoablation mode and a thermal ablation mode to provide cryoablation and thermal ablation functionality. The shell 802 and the conduit 804 can be configured similarly to the shell and conduit previously described with respect to probes 100, 200, and 300. The conduit 804 may supply a cryo-fluid to the tip 810 of the probe 800 at the distal end 808.

In this example, the first heat transfer element 812 and the second heat transfer element 814 may have arcuate shapes. The first heat transfer element 812 and the second heat transfer element 814 may each be configured as a truncated portion of ring such that each element is positioned in a portion of the annular space between the outer surface of the conduit 804 and the inner surface of the shell 802. The first heat transfer element 812 and the second heat transfer element 814 may each be positioned at different circumferential orientations at their respective axial positions. The offset positions of the first heat transfer element 812 and the second heat transfer element 814 can permit the cryo-fluid to flow through a return path away from the distal end 808 of the probe 800. The offset positions of the first heat transfer element 812 and the second heat transfer element 814 may also provide improved stability to the probe 800.

As best shown in FIG. 9, the first heat transfer element 812 may be heated by a first heater 824 and the second heat transfer element 814 may be heated by a second heater 822. The first heater 824 can be coiled around the first heat transfer element 812. The second heater 822 may be similarly coiled around the second heat transfer element 814. Each of the first heat transfer element 812 and the second heat transfer element 814 may include grooves, recessed portions, or other features to retain the first heater 824 and/or the second heater 822 in position. Additionally or alternatively, the first heater 824 and/or the second heater 822 can be retained in position with adhesive or epoxy.

Figure 10:
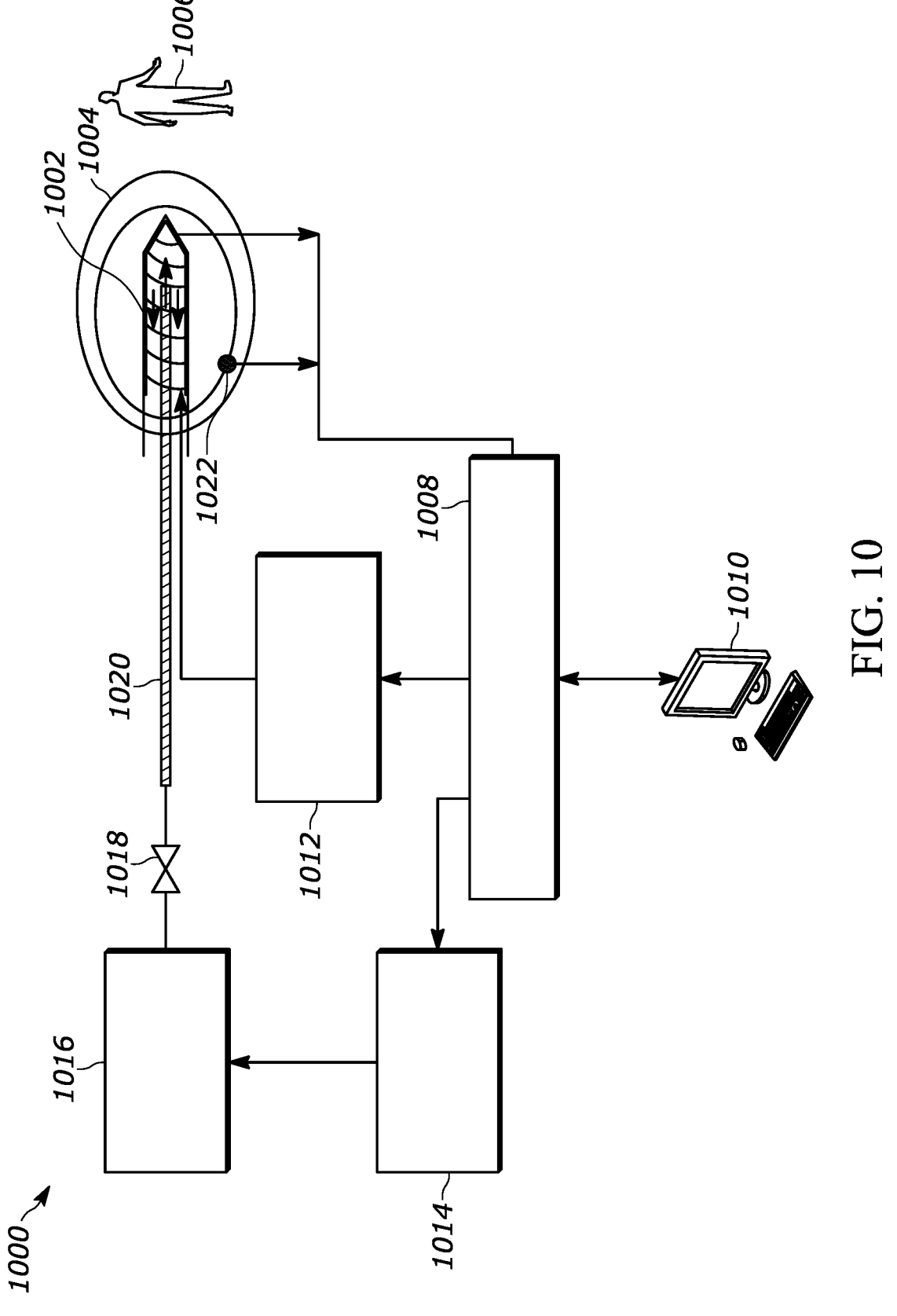
FIG. 10 is a diagram illustrating an example ablation system that can be used with the example ablation probes of the present disclosure.

Turning now to FIG. 10, and example combination ablation system 1000 is shown. The cryoablation system 1000 may include a cryoablation computing device 1010, a combination control 1008, a cryo-fluid pump 1014, a cryo-fluid source 1016, an inlet valve 1018, a cryo-fluid supply 1020, a combination probe 1002, and a controllable power supply 1012. The cryo-fluid pump 1014, the cryo-fluid source 1016, the inlet valve 1018, the cryo-fluid supply 1020, the combination probe 1002 may operate to deliver a cryo-fluid from the cryo-fluid source 1016 to the probe 1002 to perform a cryoablation cycle in one mode of operation. The cryo-fluid (e.g., liquid nitrogen) can be stored in the cryo-fluid source 1016, such as a dewar or other suitable container, and then delivered to the probe 1002 via the cryo-fluid supply 1020. The cryo-fluid may expand at a tip of the probe 1002 and cool the tip of the probe 1002 to a temperature at which the tissue of a patient 1006 begins to freeze forming an ice ball 1004. The probe 1002 can be positioned at or near a target tissue (e.g., a tumor) in the patient. In this manner, the target tissue can be frozen destroying the target tissue.

The combination ablation system 1000 can also be operated in a second mode of operation to perform a thermal ablation treatment. The second mode of operation can also be used to perform a thaw cycle, a coagulation cycle, a cauterization cycle, or other cycle in which the probe 1002 is heated. The power supply 1012 can be used to energize a heater located internal to the probe 1002. The probe 1002 can include a structure as previously described to cause heat from the heater in the probe 1002 to conduct heat to the shell of the probe 1002. The probe 1002 may be used to reach temperatures greater than 150° C. in some examples, and greater than 200° C. in other examples.

The combination ablation system 1000 is an improvement over existing or traditional systems in that the system can be operated in either mode of operation to perform cryo cycles and thermal cycles repeatedly using a single probe. The system 1000 can perform cryoablation treatments, thermal ablation treatments, or both during a single procedure. Such flexibility and functionality can allow ablation treatment to be performed during a single procedure to improve treatment effectiveness. Furthermore, the thermal cycles can also be performed more quickly than coagulation cycles or thaw cycles using traditional system of probes because the probe 1002 can be heated more quickly. An example ablation probe similar to the probe 1002 was tested for a thaw cycle and compared to an existing probe. The existing probe (that did not include the structure of the probes of the present disclosure) was able to be removed from an ice ball in a time of about 40 seconds. The example probe with the internal resistance heater and the heat transfer elements as described above was able to be removed from the ice ball in about 20 to about 25 seconds after the thaw cycle was initiated. Thus, the ablation probes of the present disclosure are able to perform thermal cycles in about 50% less time than existing probes.

A treatment plan can be determined prior to the performance of an ablation treatment. The treatment plan can detail and/or describe the various steps of the process and various aspects of the treatment such as the types of equipment to be used, a positioning of the probe, temperatures of the probe, duration of cryo and thermal cycles as well as a quantity of cycles. The treatment plan may be determined by a medical professional and/or by others. In some examples, the ablation computing device 1010 may determine or recommend a treatment plan after health, patient, and other information is input into the ablation computing device 1010 or is retrieved or otherwise obtained by the ablation computing device 1010.

As further shown in FIG. 10, the control 1008 may be coupled to the probe 1002 and/or a sensor 1022. The control 1008 may collect measurement data from the probe 1002 and/or the sensor 1022 regarding temperatures of the target tissue and/or temperatures of the probe 1002 during a treatment. The probe 1002, in this example, may include multiple impedance sensors or measuring devices. The impedance measurements from these impedance sensors can be used to determine a temperature, or other condition of the patient, such as a bleeding condition. The sensor 1022 may be any suitable sensor such as an impedance sensor, temperature sensor, or the like. The measurement data from the sensor 1022 and/or the probe 1002 can be sent to the control 1008 and/or the computing device 1010 and stored or processed as needed.

The control 1008 can be any suitable controller, PLC, data acquisition unit or other control unit. The control 1008 is operable not only to receive impedance and/or other measurement signals from the other elements of the ablation system 1000 but may also be operable to control, change or adjust operating parameters of the ablation system 1000. For example, the control 1008 may be operable to control the power supply 1012 to energize the heater in the probe 1002. The control 1008 may change, adjust or control the voltage, current, power profile, frequency and timing of the power delivered to the heater in the probe 1002. Such control can be used, for example, to manage thermal cycles of the ablation system 1000.

The control 1008 is also coupled to the cryo pump 1014 and other elements of the ablation system 1000 that operate the flow of cryo-fluid to the probe 1002 during a cryo cycle. The control 1008 can operate to manage and control the flow of cryo-fluid and the operating conditions of the cryo-fluid to create the ice ball 1004 to form during a cryo cycle.

The computing device 1010 can be any suitable computing device that can operate to receive and process data and provide instructions to the control 1008. The computing device 1010 may be, for example, a suitable workstation, computer, laptop, tablet, server or the like.

Figure 11A:
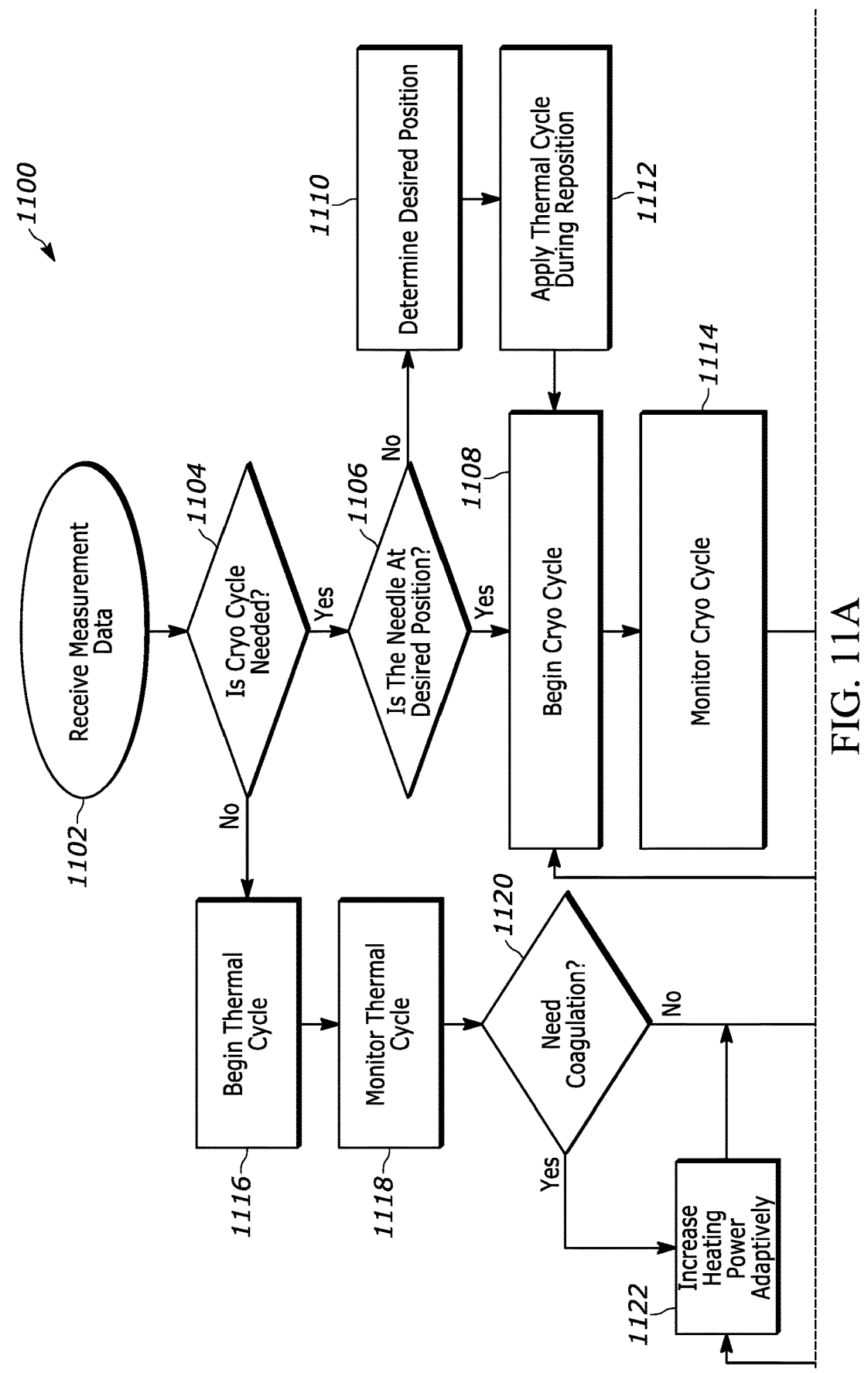
FIGS. 11A and 11B is a flow chart illustrating an example method of performing an ablation procedure.
Figure 11B:
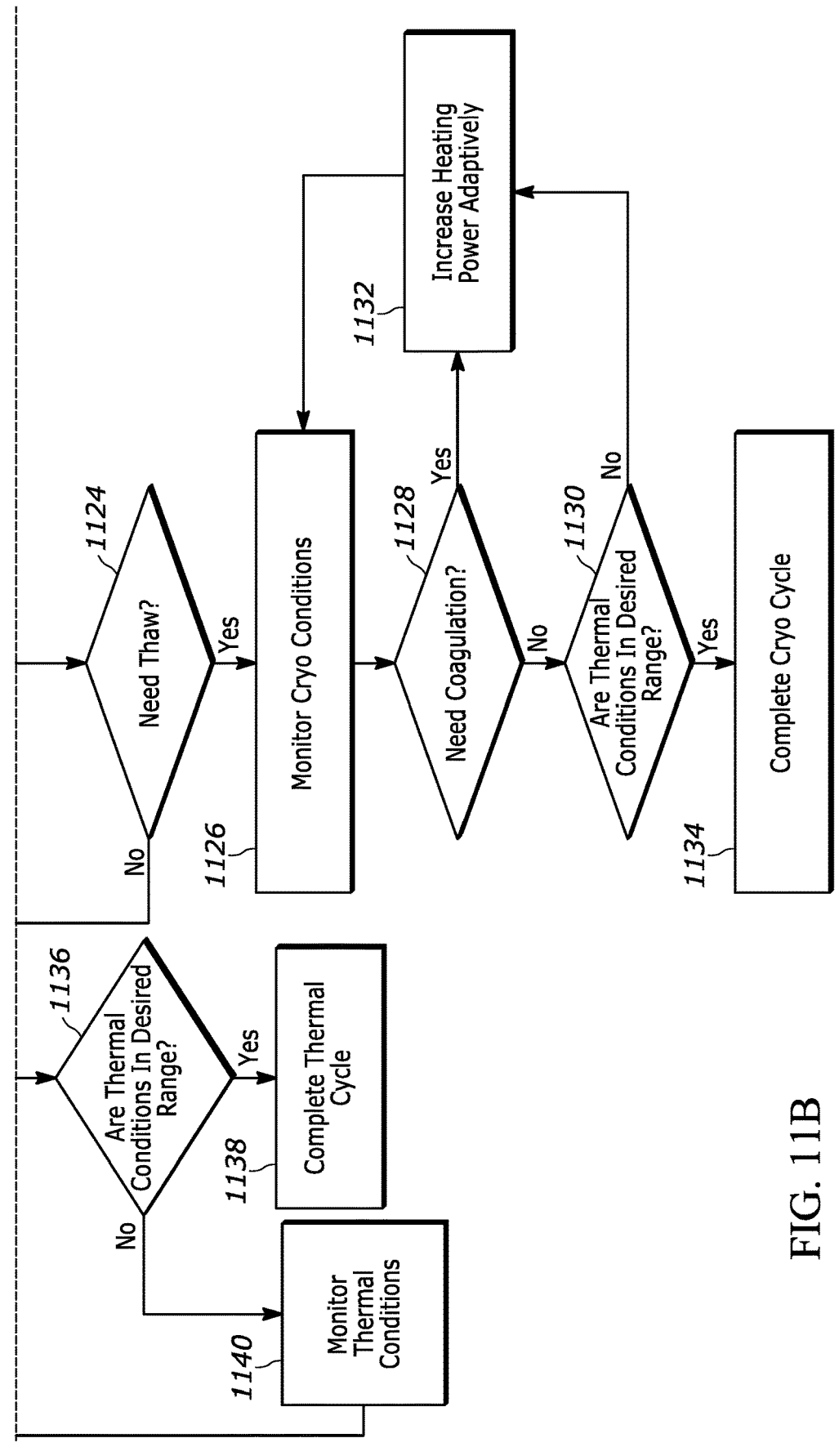

Referring now to FIG. 11, an example method 1100 of performing an ablation procedure is shown. The method 1100 may be performed using the combination ablation system 1000 previously described. Other systems and apparatuses may also be used. The description below describes the method 1100 being performed by the system 1000 but it should be appreciated that other systems and apparatuses can also be used.

The method 1100 may begin at step 1102. At step 1102, measurement data is received. The measurement data may be received from various sensors, the probe or elsewhere regarding conditions of the patient and of elements of the ablation system 1000. The measurement data may be used to determine whether conditions are in desired operating ranges and/or the patient conditions are in proper ranges to begin an ablation treatment. Such measurement data may be compared with a treatment plan or other information that is obtained by the computing device 1010.

At step 1104, it is determined whether a cryo cycle is needed. The computing device 1010 may have obtained a treatment plan and such plan may indicate whether a cryo cycle is needed. In other circumstances, a medical professional may determine whether a cryo cycle is needed. If a cryo cycle is needed, the method 1100 may proceed to step 1106. If a cryo cycle is not needed, the method 1100 may proceed to step 1116.

At step 1106, the computing device 1010 may determine if the needle of the ablation probe is at a desired position. In other examples, a medical professional may determine if the needle of the ablation probe is at the desired position. Imaging may be performed and such images may be obtained by the computing device 1010. The images may be compared to a pre-treatment image and/or to the treatment plan to determine if the probe is positioned at or near the target tissue. There may be other body structures near the target tissue and the probe's position to these other body structures may be determined before an ablation cycle is performed. If the probe is positioned at a desired position, the method 1100 moves to step 1108. If the probe is not positioned at a desired position, the method 1100 moves to step 1110.

At step 1110, a new desired position may be determined. In some examples, the computing device 1010 may determine the new desired position. In other examples, a medical professional may make such determination. The new desired position may be indicated in the treatment plan. The computing device 1010 may determine, for example, that the probe needs to be retracted, re-positioned, or otherwise moved in order to position the probe in a desired location relative to the target tissue and/or positioned away from a neighboring body structure such as a blood vessel.

At step 1112, the computing device 1010 and/or the control 1008 may cause a thermal cycle to be initiated during re-positioning of the probe. It may be desirable to initiate a thermal cycle so that cauterization can be performed during re-positioning. Such a cautery thermal cycle may be desirable because the probe may have contacted undesirable cells, such as cancer cells. The cautery thermal cycle can reduce a likelihood that the undesirable cells are moved or migrated to another location in the patient. The cautery thermal cycle may also reduce a likelihood of bleeding during the re-positioning.

The cautery thermal cycle may be initiated by the control 1008 that can cause a power signal from the power supply 1012 to be supplied to the heater in the probe 1002. The power signal may be in the range of about 40 to about 50 Watts (W), for example. The cautery thermal cycle may also have a predetermined duration. In some examples, the cautery thermal cycle may have a duration of about 15 to about 120 seconds. In other examples, other durations may be used. The method 1100 may then proceed to step 1108.

At step 1108, the computing device 1010 and/or control 1008 may begin a cryo cycle. The control 1008 may cause cryo-fluid to be supplied to the probe 1002 at a predetermined temperature and pressure. Such flow can cause an ice ball to form at the distal end of the probe 1002. The method 1100 may then proceed to step 1114.

At step 1114, the ablation system 1000 may monitor the cryo cycle. During such monitoring, measurement data may be collected regarding the ablation conditions at the probe 1002 and/or of the patient 1006. For example, temperature, pressure, flow rate, ice ball size, ice ball growth or the like can be collected and compared against predetermined thresholds or predetermined ranges by the computing device 1010. The predetermined ranges, thresholds or other operating parameters may be determined prior to the treatment being performed. Such information may be obtained in a treatment plan, for example. The treatment may also include information regarding a number and duration of cryo and/or thermal cycles that are to be performed. This information can be compared to the information and/or measurement data obtained at step 1114. After step 1114, the method 1100 may proceed to step 1124.

At step 1124, the computing device 1010 and/or the control 1008 may determine whether a thaw cycle is needed. The thaw cycle may be prescribed or included in the treatment plan. In other circumstances, the computing device 1010 and/or operator may determine that a thaw cycle is needed. A thaw cycle may be needed, for example, if the cryo cycle has ended, the probe is to be withdrawn or the size of the ice ball is growing too fast or too large than may be needed or desired. If the computing device 1010 (or user) determines that a thaw cycle is needed, the method may proceed to step 1126. If it is determined that a thaw cycle is not needed, the method 1100 may proceed back to step 1108, wherein the cryo cycle is continued or repeated until such time that a thaw cycle is needed.

At step 1126, the heater of the probe may be energized to heat the probe and the conditions of the cryo cycle are continued to be monitored. The power that is supplied at step 1126 may be adjusted, changed, or maintained depending on the measurement data that is obtained by the control 1008 and/or the computing device 1010. The temperature of the probe, impedance, and/or size of the ice ball may be monitored and compared to thresholds or ranges as previously described. The control 1008 may take action to cause the probe to heat as desired in order for conditions to be maintained or achieved as desired.

At step 1128, the computing device 1010 may determine whether a coagulation cycle is needed. The computing device 1010 may receive impedance measurement from the probe and/or other sensor in the region of the treatment. The impedance, for example, may provide an indication of whether a bleeding condition is present. The computing device 1010 may determine that a coagulation cycle is needed if the measurement data indicates that a bleeding condition is present. If a coagulation cycle is needed, the method may proceed to step 1132. If no coagulation cycle is needed, the method 110 may proceed to step 1130.

At step 1132, the computing device 1010 and/or the control 1008 may increase heating power to the heater in the probe. The control 1008 may send an instruction to the power supply 1012 to increase the power supplied to the heater. The control 1008 and/or the computing device 1010. The power may be increased, for example, until the temperature of the probe achieves a predetermined temperature threshold or a predetermined temperature range. The method 1100 may then return to step 1126 to repeat steps 1126 and 1128.

At step 1130, the thermal conditions of the probe and/or the patient may be monitored. The probe may be removed from the target tissue and/or the ice ball at this stage of the cryo cycle after all cycles (e.g., cryo and/or thermal) have been completed. The system may continue to monitor the thermal conditions to determine if a bleeding condition is present. In other circumstances, it may be desirable to perform a cautery cycle if the probe is being removed. Such a cautery cycle can prevent or reduce the likelihood of a bleeding condition when the probe is removed. If such additional heating is desired and/or needed, the method may proceed to step 1132. At step 1132, the control 1008 and/or the computing device 1010 may increase power to the heater in the probe to increase heating to perform a coagulation or cautery cycle as may be desired. If the thermal conditions are in desired ranges and the duration and quantity of cryo and/or thermal cycles is complete, the method 1100 may move to step 1134 where the cryo cycle is complete. While not shown, the method may move back to the start to perform more cryo cycles as may be desirable for particular ablation treatments.

As previously discussed, at step 1104, the computing device 1010 may determine that a cryo cycle is not needed. The computing device 1010 may determine that a thermal cycle is needed. The treatment plan or medical professional may determine that a thermal cycle is needed in other examples. A thermal cycle may begin at step 1116. To begin the thermal cycle, the computing device 1010 and/or control 1008 may cause the power supply 1012 to deliver a power signal to the heater in the probe. This may cause the shell of the probe to begin to heat as heat is transferred from the heater to the probe shell.

The method 1100 may then move to step 1118. At step 1118, the computing device 1010 and/or control 1008 may monitor the thermal cycle. Measurement data that include impedance information, temperature information, power information, patient information, and the like may be received and monitored by the computing device 1010 as previously described. The measurement data may be compared to predetermined thresholds and/or predetermined ranges in order to achieve a desired result such as the thermal ablation of a target tissue in the patient. As such, the probe may reach temperatures in excess of 150° C. In other examples, the probe may reach temperatures in excess of 200° C.

At step 1120, the computing device 1010 may determine whether a coagulation cycle is needed. The coagulation cycle at step 1120 may be performed if a bleeding condition is detected. The coagulation cycle at step 1120 may be performed similarly to step 1128 previously described. If a coagulation cycle is needed the method may proceed to step 1122 where power is adjusted to achieve a desired temperature to promote coagulation. If no coagulation is needed, the method 1100 may proceed to step 1136.

At step 1136, the computing device 1010 and/or the control 1008 may monitor the thermal conditions to determine if the conditions are in the desired range(s). The computing device 1010 may determine this by receiving the measurement data and comparing the measurement data to predetermined thresholds or predetermined ranges. If the thermal conditions indicate, the thermal cycle has achieved the predetermined limits, thresholds, and/or ranges, the thermal cycle may proceed to step 1138 at which time the thermal cycle may end. The limits, thresholds and/or ranges may include duration, temperature, impedance, and the like. If the computing device determines that thermal conditions have not achieved the cycle requirements, the method 1100 may move to step 1140 at which time the computing device can continue to monitor the thermal conditions and to adjust the power to the heater in the probe at step 1122 as may be necessary to achieve the cycle requirements.

As with the previously described cryo cycle, the thermal cycle in method 1100 may be repeated a suitable number of times as may be desired. Thermal cycles and cryo cycles may be alternated, repeated, or varied to achieve a desired result during an ablation treatment.

Figure 12:
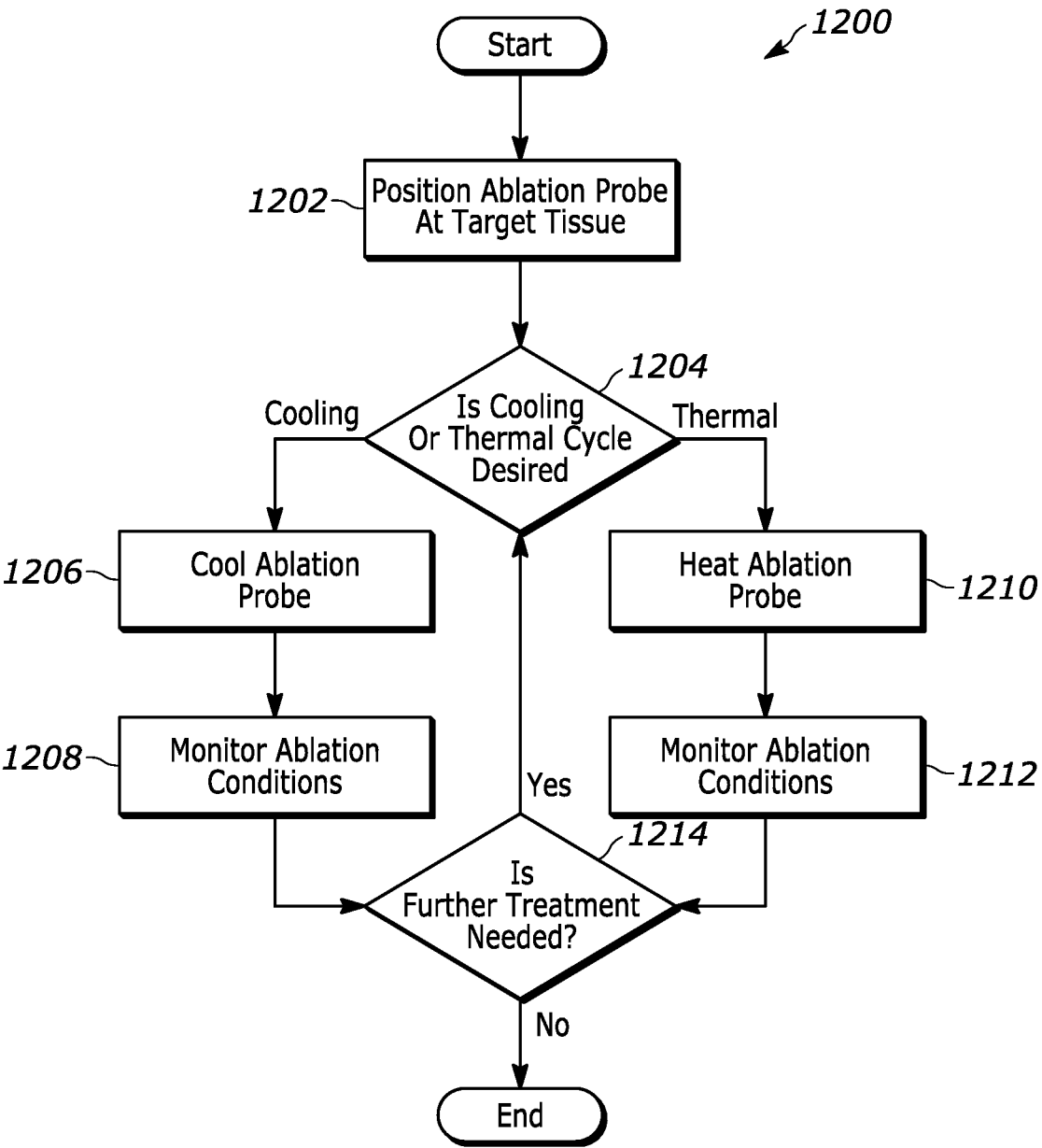
FIG. 12 is a flow chart illustrating another example method of performing an ablation procedure.

Another example method 1200 of performing an ablation treatment is shown in FIG. 12. The method 1200 is described below with reference to the ablation system 1000 but it should be appreciated that other systems and apparatuses can also be used to perform some or all the steps of method 1200.

The method 1200 may begin at step 1202. At step 1202, an ablation probe is positioned at a target tissue in a patient. The probe may be positioned by a medical professional, robotic tool, or other suitable device using image data that may be obtained during or prior to the ablation treatment. The probe that is inserted at the target tissue is a combination probe such as the combination probes of the present disclosure. The combination probe may include an internal heater. The combination probe can be operated to perform a cryo ablation cycle and a thermal ablation cycle.

The method 1100 then may proceed to step 1204. At step 1204, the computing device 1010 and/or control 1008 may determine whether a cooling or thermal cycle is desired. A medical professional may indicate which cycle to perform using an input device to the computing device 1010, in some examples. In other examples, the treatment plan may indicate a quantity and order of thermal and cryo cycles that are to be performed during an ablation treatment. The computing device 1010 may obtain the treatment plan and then perform the ablation treatment accordingly. If a cryo cycle is desired the method 1200 may proceed to step 1206. If a thermal cycle is desired, the method 1200 may proceed to step 1210.

At step 1206, the computing device 1010 and/or the control 1008 may cause the ablation probe to be cooled. This may be performed by the control 1008 that may send signals to the pump 1014, the valve 1018, and/or the cryo-fluid source 1016 to cause the cryo-fluid to flow to the probe 1002. The cryo-fluid may be circulated through the probe 1002 to cause the ice ball 1004 to be formed at the target tissue.

At step 1208, the ablation conditions of the cryo cycle may be monitored. The computing device 1010 and/or the control 1008 may receive measurement data from the probe or other sensors as previously described. While not shown, the operating condition of the system 1000 may be adjusted, adapted or otherwise controlled during the cryo cycle to maintain the ablation conditions in a predetermined range or to reach a predetermined threshold. Once these ablation conditions are achieved, the method 1200 may proceed to step 1214.

At step 1214, the computing device 1010 and/or the control 1008 may determine whether further treatment is needed. The computing device may determine, for example, that another cryo cycle is needed. In other examples, the computing device 1010 may determine that a thermal cycle is needed. If further treatment is needed, the method 1200 can return to step 1204 and re-perform the steps of method 1200.

If a thermal cycle is desired, the method 1200 moves to step 1210. At step 1210, the probe is heated. The computing device 1010 and/or the control 1008 may cause the power supply 1012 to supply a power signal to the heater in the probe 1002. This may cause the probe 1002 to heat at its location. The thermal cycle may be used to perform a thaw cycle (i.e., to remove the probe from the ice ball), to perform a coagulation cycle if a bleeding condition is detected, to perform a cautery cycle if the probe is to be moved or removed from the ablation site, or to perform an ablation cycle to destroy a target tissue. The control 1008 can change, adapt, and/or control the power that is delivered to the heater in the probe to achieve a desired temperature that may be needed depending on the type of thermal cycle that is desired.

At step 1212, the computing device 1010 and/or the control 1008 may monitor the ablation conditions. The computing device 1010 and/or the control 1008 may receive measurement data and/or other information as previously described. While the thermal cycle is being performed, the computing device 1010 and/or the control 1008 may adjust, change, or control the operating conditions of the system 1000 to achieve desired conditions for the thermal cycle.

At step 1214, the computing device 1010 and/or the control 1008 may determine whether further treatment is needed. The method 1200 may return to step 1204 to re-perform thermal or cryo cycles as may be desired. If further treatment is not required, the method 1200 may end.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An ablation probe comprising:
   a shell configured to be positioned at a target tissue in a patient;
   a conduit positioned inside the shell, the conduit configured to supply a cryo-fluid toward a tip;
   a heater positioned radially outward of the conduit in the shell; and
   at least one heat transfer element in thermal communication with the heater and the shell and contacting the heater and the shell.

2. The ablation probe of claim 1, wherein the at least one heat transfer element is positioned radially outward of the conduit and radially inward of the shell.

3. The ablation probe of claim 1, wherein the conduit includes at least one opening at or near the tip to allow cryo-fluid to exit the interior of the conduit and flow in a return direction between an outer surface of the conduit and an inner surface of the shell.

4. The ablation probe of claim 3, wherein the at least one heat transfer element is positioned on the outer surface of the conduit spaced axially from the at least one opening of the conduit.

5. The ablation probe of claim 1, wherein the at least one heat transfer element is directly in contact with the heater and a distal end of the tip.

6. The ablation probe of claim 1, wherein the at least one heat transfer element is positioned in direct contact with the heater and the shell.

7. The ablation probe of claim 1, wherein the at least one heat transfer element comprises a conical plug positioned at the tip.

8. The ablation probe of claim 1, wherein the at least one heat transfer element comprises an annular member positioned at a predetermined axial location along an outer surface of the conduit.

9. The ablation probe of claim 8, wherein conductive portions of the annular member contact an inner surface of the shell, the conductive portions spaced apart from each other around a circumference of the annular member to define return pathways for the cryo-fluid to flow away from the tip toward a proximal end of the ablation probe.

10. The ablation probe of claim 1, wherein the at least one heat transfer element comprises a plurality of annular members positioned along an outer surface of the conduit and each annular member of the plurality of annular members is spaced apart from an adjacent annular member.

11. The ablation probe of claim 1, wherein the heater comprises a resistive heating coil.

12. The ablation probe of claim 11, wherein the resistive heating coil is in direct contact with the heat transfer element and is not in direct contact with the shell.

13. The ablation probe of claim 1, wherein the heater is coiled around the at least one heat transfer element.

14. The ablation probe of claim 13, wherein the at least one heat transfer element comprises an arcuate shaped member positioned around a portion of an outer circumference of the conduit.

15. The ablation probe of claim 1, wherein the at least one heat transfer element comprises a first arcuate shaped member and a second arcuate shaped member positioned at different axial positions on the conduit.

16. An ablation probe comprising:

an outer shell;

an inner conduit axially aligned with the outer shell and positioned radially inside the shell;

a first annular heat transfer element positioned at a first axial location, the first annular heat transfer element having an outer profile comprising contacting portions that contact an inner surface of the outer shell and non-contacting portions that are spaced apart from the inner surface of the outer shell;

a second annular heat transfer element positioned at a second axial location, the second annular heat transfer element oriented generally parallel to the first annular heat transfer element; and a heater positioned inside the shell in contact with the first annular heat transfer element and the second heat transfer element.

17. A method of performing an ablation treatment comprising:

positioning the ablation probe of claim 1 at or near a target tissue in a patient;

cooling the ablation probe using a cryo-fluid circulated through the ablation probe to cause an ice ball to be formed at the target tissue; and heating the ablation probe using a heater positioned inside the ablation probe to cause tissue at or near the target tissue to be destroyed.

18. The method of claim 17, wherein the step of heating the ablation probe comprises heating the ablation probe to a temperature greater than or equal to 150° C.

19. The method of claim 17, wherein the ablation probe is not moved after the ablation probe is positioned at or near the target tissue to perform the cooling and heating steps.

20. The method of claim 17, wherein the step of heating the ablation probe is performed by energizing the heater and conducting heat from the heater through a heat transfer element to an outer shell of the ablation probe.

* * * * *